(12) United States Patent
Liphardt et al.

(10) Patent No.: US 9,442,016 B2
(45) Date of Patent: Sep. 13, 2016

(54) REFLECTIVE FOCUSING OPTICS

(71) Applicant: J.A. WOOLLAM CO., INC, Lincoln, NE (US)

(72) Inventors: Martin M. Liphardt, Lincoln, NE (US); Jeffrey S. Hale, Lincoln, NE (US); Ping He, Lincoln, NE (US); Galen L. Pfeiffer, Roca, NE (US)

(73) Assignee: J.A. WOOLLAM CO., INC, Lincoln, NE (US)

( * ) Notice: Subject to any disclaimer, the term of this patent is extended or adjusted under 35 U.S.C. 154(b) by 197 days.

(21) Appl. No.: 14/121,915

(22) Filed: Nov. 4, 2014

(65) Prior Publication Data
US 2015/0355029 A1  Dec. 10, 2015

Related U.S. Application Data

(60) Provisional application No. 61/997,589, filed on Jun. 6, 2014.

(51) Int. Cl.
| | |
|---|---|
| *G01J 4/00* | (2006.01) |
| *G01J 4/04* | (2006.01) |
| *G02B 19/00* | (2006.01) |
| *G01J 1/04* | (2006.01) |
| *G01N 21/21* | (2006.01) |

(52) U.S. Cl.
CPC ............ *G01J 4/04* (2013.01); *G01J 1/0411* (2013.01); *G01J 1/0414* (2013.01); *G01J 4/00* (2013.01); *G01N 21/21* (2013.01); *G02B 19/0023* (2013.01)

(58) Field of Classification Search
CPC ............ G01J 4/00; G01J 4/04; G01J 1/0411; G01J 1/0414; G01N 21/21
USPC ............................................. 356/369
See application file for complete search history.

(56) References Cited

U.S. PATENT DOCUMENTS

| | | | |
|---|---|---|---|
| 4,790,659 A | 12/1988 | Erman et al. | 356/369 |
| 5,048,970 A | 9/1991 | Milosevic et al. | 356/445 |
| 5,608,526 A | 3/1997 | Piwonka-Corle et al. | 356/369 |
| 5,798,837 A | 8/1998 | Aspnes et al. | 356/369 |
| 5,917,594 A | 6/1999 | Norton | 356/327 |
| 5,969,818 A * | 10/1999 | Johs | G01J 3/447 356/364 |
| 6,549,282 B1 | 4/2003 | Johs et al. | 356/369 |
| 6,600,560 B2 | 7/2003 | Mikkelsen et al. | 356/369 |
| 6,734,967 B1 | 5/2004 | Piwonka-Corle et al. | 356/369 |
| 6,795,185 B2 | 9/2004 | Yoshizawa et al. | 356/369 |
| 6,804,004 B1 * | 10/2004 | Johs | G01J 3/14 356/369 |
| 6,819,423 B2 | 11/2004 | Stehle et al. | 356/369 |
| 6,829,049 B1 | 12/2004 | Uhrich et al. | 356/369 |
| 6,859,278 B1 | 2/2005 | Johs et al. | 356/369 |
| 6,943,880 B2 | 9/2005 | Kanzaki | 356/369 |
| 7,095,498 B2 | 8/2006 | Horie | 356/364 |
| 7,130,039 B2 | 10/2006 | Vaez-Iravani et al. | 356/237.5 |
| 7,158,231 B1 | 1/2007 | Woollam et al. | 356/369 |
| 7,184,145 B2 | 2/2007 | Amary et al. | 356/369 |
| 7,215,424 B1 | 5/2007 | Liphardt et al. | 356/369 |

(Continued)

*Primary Examiner* — Roy M Punnoose
(74) *Attorney, Agent, or Firm* — James D. Welch

(57) ABSTRACT

A reflective optics system that preferably requires the presence of both convex and a concave mirrors that have beam reflecting surfaces, the application of which achieves focusing of a beam of electromagnetic radiation onto a sample, (which can be along a locus differing from that of an input beam), with minimized effects on a polarization state of an input beam state of polarization based on adjusted angles of incidence and reflections from the various mirrors involved.

18 Claims, 4 Drawing Sheets

(56) References Cited

U.S. PATENT DOCUMENTS

| | | | |
|---|---|---|---|
| 7,248,364 B2 | 7/2007 | Hebert et al. | 356/369 |
| 7,265,838 B1 | 9/2007 | Johs et al. | 356/369 |
| 7,277,171 B1 | 10/2007 | Johs et al. | 356/369 |
| 7,289,219 B2 | 10/2007 | Norton et al. | 356/445 |
| 7,336,361 B1 | 2/2008 | Liphardt et al. | 356/369 |
| 7,359,052 B2 | 4/2008 | Fielden et al. | 356/369 |
| 7,369,233 B2 | 5/2008 | Nikoonahad et al. | 356/369 |
| 7,505,133 B1 | 3/2009 | Zawaideh et al. | 356/369 |
| 7,505,134 B1 | 3/2009 | Johs et al. | 356/369 |
| 7,616,319 B1 | 11/2009 | Woollam et al. | 356/451 |
| 7,633,625 B1 | 12/2009 | Woollam et al. | 356/451 |
| 7,746,471 B1 | 6/2010 | Johs et al. | 356/369 |
| 7,746,472 B1 | 6/2010 | Johs et al. | 356/369 |
| 7,860,040 B2 | 12/2010 | Thill et al. | 370/314 |
| 8,030,632 B2 | 10/2011 | Norton et al. | 250/559.08 |
| 8,767,209 B2 | 7/2014 | Li et al. | 356/369 |

\* cited by examiner

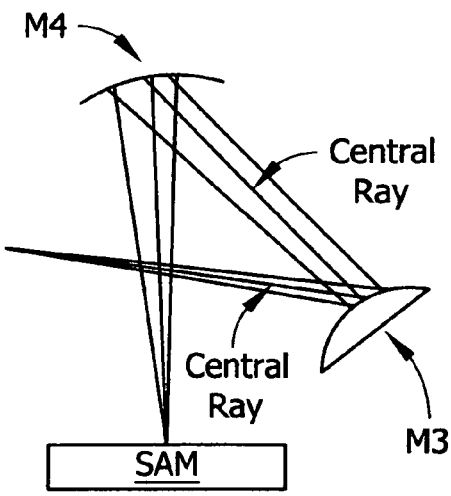
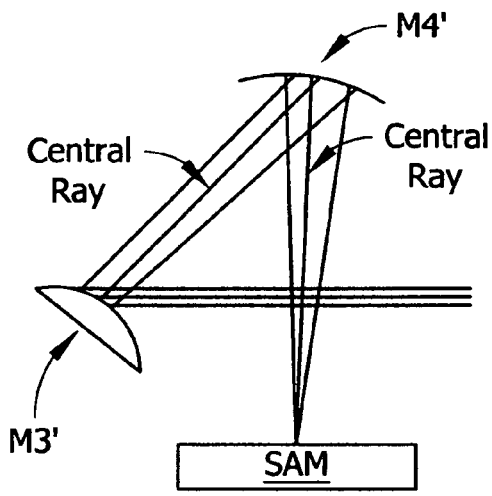
FIG. 2a
FIG. 2b
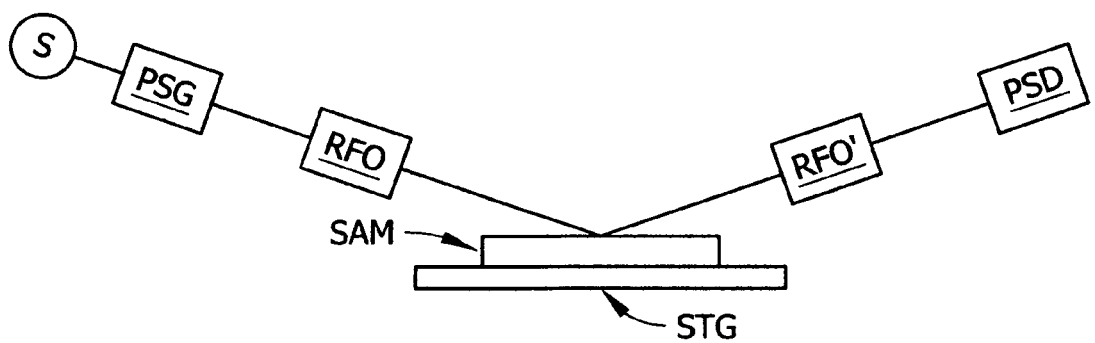
FIG. 3a
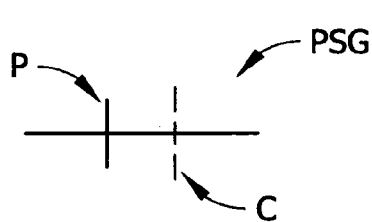
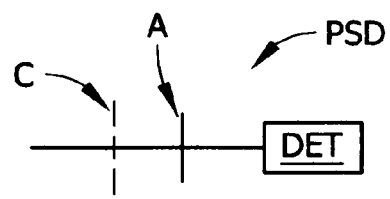
FIG. 3b
FIG. 3c

REFLECTIVE FOCUSING OPTICS

This Application Claims Benefit of Provisional Application Ser. No. 61/997,589 Filed Jun. 6, 2014.

TECHNICAL FIELD

The present invention relates to focusing beams of electromagnetic radiation onto samples, and more particularly to a reflective optics system that requires the presence of both convex and a concave mirrors that have beam reflecting surfaces. Application thereof achieves focusing of a beam of electromagnetic radiation with minimized effects on a polarization state of an input beam state of polarization that results from adjustment of angles of incidence and reflections from the various mirrors involved.

BACKGROUND

It is known to focus beams of electromagnetic radiation onto samples, such as in the practice of ellipsometry, and said focusing can be achieved using refractive or reflective optics. Numerous Patents provide insight this in general, but a particularly relevant one is U.S. Pat. No. 5,969,818 to Johs et al. This Patent is specifically disclosed as it describes a "Beam Folding Optics", (best shown in FIG. 5 thereof), that comprises four similar mirrors oriented such that reflections from the first and second thereof define a plane of incidence that is substantially orthogonal to a plane of incidence formed by reflections for the third and fourth thereof. The result of applying said Beam directing Optics is to direct a beam of electromagnetic radiation, in a desired direction that is other than along a locus of a beam input to said system, but because of polarization state change cancellation effects of reflections from the first two mirrors, and reflections from the last two mirrors, the system has essentially no effect on the polarization state of a beam exiting said Beam Folding Optics, as compared to that of a beam input thereto. Other Patents that describe the "Beam Folding Optics" are: U.S. Pat. Nos. 7,746,472; 7,746,471; 7,633,625; 7,616,319; 7,505,134; 7,336,361; 7,265,838; 7,277,171; 7,265,838; 7,215,424; 7,158,231; 6,859,278; 6,822,738; 6,804,004; and 6,549,282. Another, very recent Patent to Li et al., U.S. Pat. No. 8,767,209, is disclosed as it describes forming angles between incoming and reflected beams of electromagnetic radiation. This is very different from forming angles between planes formed by two sets of incoming and reflected beams, however, as is done in the Present Invention. Additional Patents are further disclosed primarily as they describe beam focusing using mirrors. Said additional Patents are: U.S. Pat. Nos. 4,790,659; 5,048,970; 5,608,526; 5,798,837; 5,917,594; 6,600,560; 6,734,967; 6,795,185; 6,819,423; 6,829,049; 6,943,880; 7,095,498; 7,130,039; 7,184,145; 7,248,364; 7,289,219; 7,359,052; 7,369,233; 7,505,133; 7,860,040 and 8,030,632.

The present invention builds on the insight provided primarily by the 818 Patent, but adds focusing capability to the system by providing both convex and concave mirrors in a system that also utilizes the effect of substantially orthogonal planes, but does not require that four primary mirrors involved to be of similar construction.

DISCLOSURE OF THE INVENTION

The present invention is a system for providing a focused beam (FB) of electromagnetic radiation onto a location on a sample (SAM), and in particular the present invention is a reflective optics system (RFO) sequentially comprising first (M1), second (M2), third (M3) fourth (M4), fifth (M3') and sixth (M4') mirrors. Each of said four mirrors (M1) (M2) (M3 (M4) provides a reflective surface, with said third (M3) and fourth (M4), and fifth (M3') and Sixth (M4'), mirrors providing convex and concave reflective surfaces, respectively.

In use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror. The beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB). Said beam reflected from the reflective surface of said convex third (M3) mirror and that reflected from said reflective surface of said concave fourth (M4) mirror forming a second plane of incidence (P2), said first (P1) and second (P2) planes of incidence being orthogonal to one another.

The effect of said four reflections from said reflective surfaces of said four (M1) (M2) (M3) (M4) mirrors is to substantially minimize the effects of all said reflections on the specific polarization state of said input beam, and to direct said output beam (OB) and provide it as a focused beam (FB) onto said sample (SAM) at the point it impinges thereupon.

Said system can involve the first (M1) and (M2) mirrors both having flat reflecting surfaces, or at least one of the first (M1) and second (M2) mirrors has a non-flat reflecting surface, or both the first (M1) and second (M2) mirrors having non-flat reflecting surfaces.

The input beam (IB), all reflected beams and the output beam (OB) can be monochromatic or spectroscopic.

The first (P1) and second (P2) planes of incidence an be defined by central rays in the reflected beams involved.

The input (IB), and the various reflected and output (OB) beams can each be considered to consist of multiple, (typically at least 16), cross-sectional areas, and in which the calculated overall effect on polarization state of the various reflections from mirrors (M1) (M2) (M3) and (M4) is arrived at by an averaging thereof.

The angles of incidence of the electromagnetic beams approaching said third (M3) and fourth (M4) mirrors can be set to twelve (12) and twenty-four (24) degrees respectively, and the angles of incidence of the electromagnetic beams approaching said first (M1) and second (M2) mirrors can be each selected from the group consisting of:

a) less than eighteen degrees;
b) eighteen degrees; and
c) greater that eighteen degrees.

Of course the recitation of twelve (12) and twenty-four (24) degrees are only relevant examples and other angle combinations can be used, (ie. generalized O1 and O2), and the angles of incidence of the electromagnetic beams approaching said first (M1) and second (M2) mirrors can be each selected from the group consisting of:

a) less than $(\theta 1+\theta 2)/2$;
b) $(\theta 1+\theta 2)/2$ degrees; and
c) greater that $(\theta 1+\theta 2)/2$ degrees.

The present invention is also an ellipsometer comprising:
a) a source (S) of a beam of electromagnetic radiation;
b) a polarization state generator (PSG);
c) a reflective focusing optics (RFO) system comprising:
   a system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, with said third (M3) and fourth (M4) mirrors providing convex and concave reflective surfaces, respectively.

In use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror;
   and such that said beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB); said beam reflected from the reflective surface of said convex third (M3) mirror and that reflected from said reflective surface of said concave fourth (M4) mirror forming a second plane of incidence (P2), said first (P1) and second (P2) planes of incidence being orthogonal to one another.

The effect of said four reflections from said reflective surfaces of said four (M1) (M2) (M3) (M4) mirrors is to substantially minimize the effects of all said reflections on the specific polarization state of said input beam, and to direct said output beam (OB) and provide it as a focused beam (FB) onto said sample (SAM) at the point it impinges thereupon.

Said ellipsometer further comprises:
d) a stage (STG) for supporting a sample (SAM); and
e) a polarization state detector (PSD).

Said system can also further comprise additional fifth (M1'), sixth (M2'), seventh (M3') and eighth (M4') mirrors arranged in substantially mirror image locations with respect to mirrors (M1), (M2), (M3) and (M4), about a vertical plane extending from the location on the sample where the electromagnetic beam impinges thereupon, said mirrors (M1'), (M2'), (M3') ad (M4') serving to collimate and direct said beam that reflects from said sample (SAM), into a polarization state detector (PSD).

Said system can also further comprise providing of a computer system (CMP), said computer system (CMP) being programmed with a mathematical model of the system provided in step a) and sample (SAM); such that in use said source (S) of an input beam (IB) of electromagnetic radiation having a specific polarization state is caused to direct an input beam (IB) at at least one angle of incidence and at least one known polarization state, toward said first (M1) mirror, reflect therefrom and interact with said second (M2), third (M3) and forth (M4) mirrors, before reflecting from said sample (SAM) and being directed into said polarization state detector (PSD) via mirrors (M1'), (M2'), (M3') and (M4') and being detected by detector (DET) therewithin; and such that said detector (DET) outputs data into said computer in which a mathematical regression is performed to assign best fit values to parameters in said mathematical model.

Said system can also provide that said mathematical model comprises parameters to account for various selections from at least:
   surface reflectivity characteristics of the surfaces of said first (M1), second (M2), third (M3) and forth (M4) mirrors before said sample, including the effects of any thin layers thereon;
   surface reflectivity characteristics of the surfaces of said fifth (M1'), sixth (M2'), seventh (M3') and eighth (M4') mirrors after said sample, including the effects of any thin layers thereon;
   angles of incidence of said electromagnetic beam with respect to the surfaces of said first (M1), second (M2), third (M3) and forth (M4) fifth (M1'), sixth (M2'), seventh (M3') and eighth (M4') mirrors, at the location thereupon at which it impinges;
   sample surface reflectivity characteristics, including the effects of any thin layers thereon;
   angle of incidence of said electromagnetic beam to the surface of said sample;
   means for spectroscopic averaging to account for the presence of more than one wavelength in said electromagnetic beam;
   means to account for electromagnetic beam smearing to account for component deviations from a central beam component;
   polarizer, compensator and analyzer effects.

The present invention also includes a method of calibrating an ellipsometer system comprising a focusing optics (RFO) on a source (S) side of a sample (SAM) and a focusing optics (RFO') on a detector (DET) side of said sample (SAM), to provide a system that minimizes the effect of multiple beam reflections therewithin on polarization state, comprising the steps of:
   providing a system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, said first (M1) and second (M2) mirrors being selected from the group consisting of:
   a) both (M1) and (M2) are flat mirrors;
   b) one of (M1) and (M2) is not flat;
   c) both (M1) and (M2) are not flat.

Further, and said third (M3) and forth (M4) are selected from the group consisting of:
   said third (M3) and fourth (M4) mirrors provide convex and concave reflective surfaces, respectively;
   both said third (M3) and fourth (M4) mirrors providing concave reflective surfaces;
   one of said third (M3) and forth (M4) mirrors being concave and the other planar In use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror; and such that said beam reflected from the reflective surface of said first (M1) mirror is directed toward said second mirror (M2) and reflects from said reflective surface thereof toward said third (M3) mirror, from which it reflects from a location thereon toward said fourth (M4) mirror, wherefrom it is reflected by the reflective surface thereof toward said sample (SAM) as a focused (FB) outgoing beam (OB); said beam reflected from the reflective surface of said third (M3) mirror and impinging on the forth mirror, which beam reflects from said reflective surface of said fourth (M4) mirror forming a second plane of incidence (P2), said first (P1) and second (P2) planes of incidence being substantially orthogonal to one another.

The effect of said four reflections from said reflective surfaces of said four (M1) (M2) (M3) (M4) mirrors is to substantially minimize the effects of all said reflections on the specific polarization state of said input beam, and to direct said output beam (OB) and provide it as a focused beam (FB) onto said sample (SAM) at the point it impinges thereupon;

Said method further comprises providing a sample (SAM) upon which said outgoing beam (OB) impinges in use; and said method further comprises providing additional reflective optics (RFO') in the form of fifth (M1'), sixth (M2'), seventh (M3') and eighth (M4') mirrors arranged in substantially mirror image locations with respect to mirrors (M1), (M2), (M3) and (M4), about a vertical plane extending from the location on the sample where the electromagnetic beam impinges thereupon, said mirrors (M1'), (M2'), (M3') ad (M4') serving to direct said beam that reflects from said sample (SAM), into a polarization state detector (PSD) as collimated, converging or diverging.

In use a beam reflecting from said sample (SAM) reflects from fifth mirror (M1') onto said sixth mirror (M2') from which it reflects onto seventh mirror (M3') toward said eighth mirror (M4') from which it reflects then enters said polarization state detector (PSD) and the multi-element detector thereof, said incident and reflected beams with respect to mirrors (M4') and (M1') forming planes (P1)' and (P2') which are orthogonal to one another.

Said method further comprises providing a computer system (CMP), said computer system (CMP) being programmed with a mathematical model of the system and sample (SAM); and causing said source (S) of an input beam (IB) of electromagnetic radiation having a specific polarization state to direct an input beam (IB) at at least one angle of incidence and at least one known polarization state, toward said first (M1) mirror, reflect therefrom and interact with said second (M2), third (M3) and forth (M4) mirrors, before reflecting from said sample (SAM) and being directed into said polarization state detector (PSD) via mirrors (M1'), (M2'), (M3') and (M4') and being detected by a multi-element detector (DET) therewithin. As a result said multi-element detector (DET) outputs multi-wavelength data into said computer in which a mathematical regression is performed to assign best fit values to parameters in said mathematical model.

And, it is again noted that said mathematical model can comprise parameters to account for various selections from at least:
  surface reflectivity characteristics of the surfaces of said first (M1), second (M2), third (M3) and forth (M4) mirrors before said sample, including the effects of any thin layers thereon;
  surface reflectivity characteristics of the surfaces of said fifth (M1'), sixth (M2'), seventh (M3') and eighth (M4') mirrors after said sample, including the effects of any thin layers thereon;
  angles of incidence of said electromagnetic beam with respect to the surfaces of said first (M1), second (M2), third (M3) and forth (M4) fifth (M1'), sixth (M2'), seventh (M3') and eighth (M4') mirrors, at the location thereupon at which it impinges;
  sample surface reflectivity characteristics, including the effects of any thin layers thereon;
  angle of incidence of said electromagnetic beam to the surface of said sample;
  spectroscopic averaging to account for the presence of more than one wavelength in said electromagnetic beam which enter a detector element;
  electromagnetic beam smearing to account for deviations in angle-of-incidence and plane-of-incidence from a central beam component which enters a detector element;
  polarizer, compensator and analyzer effects.

It will be appreciated then that the preferred present invention method of calibrating an ellipsometer that comprises reflective optics (RFO) and (RFO'), includes both mechanical adjustments of the various components, and arriving at optimum values for parameters in a mathematical model of the system As it is an important embodiment, it is noted that in the above, mirrors (M3) and (M3') can convex and the beam of electromagnetic radiation reflecting therefrom be from an off-center location thereupon.

The present invention will be better understood by reference to the Detailed Description Section of this Specification, in combination with the Drawings.

BRIEF DESCRIPTION OF THE DRAWINGS

FIG. 2a shows that the off-center reflection from the third convex mirror (M3) provides a "spread-out" beam incident onto the concave fourth (M4) mirror, which fourth (M4) concave mirror serves to focus the spread-out beam onto a sample (SAM) as focused beam (FB).

FIG. 2b shows an arrangement for use on the Detector (DET) side of the Sample which compliments that arrangement on the Source (S) side.

FIG. 3a shows an ellipsometer system of the present invention which includes the reflective focusing optics (RFO) (RFO').

FIG. 3b demonstrates typical components of a Polarization State Generator (PSG) as a Polarizer (P), and optionally a Compensator (C).

FIG. 3c demonstrates typical components of a Polarization State Detector (PSD) as an Analyzer (A), and optionally a Compensator (C) and a multi-element Detector (DET).

DETAILED DESCRIPTION

Figure 1A:
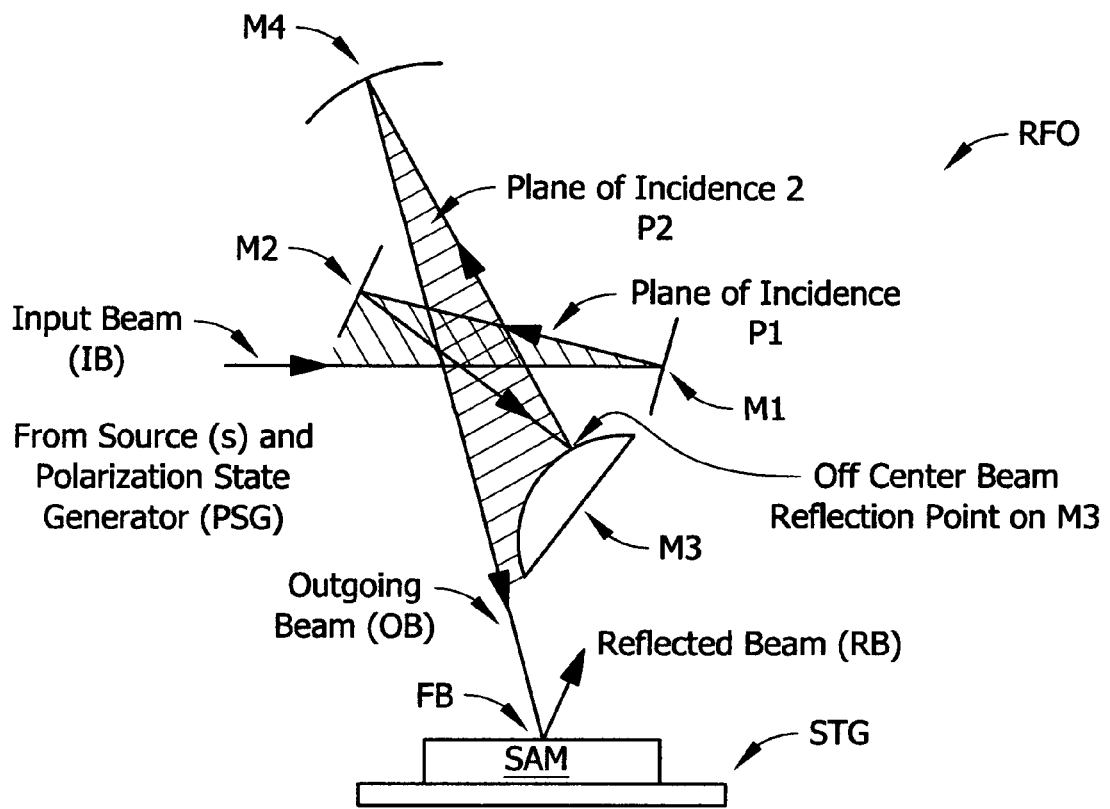
FIG. 1a shows a system for providing a focused beam (FB) of electromagnetic radiation onto a location on a sample (SAM) with minimal change of polarization state therein.

Turning now to FIG. 1a, there is shown a system for providing a focused beam (FB) of electromagnetic radiation onto a location on a sample (SAM), and in particular the present invention is a reflective optics system (RFO) sequentially comprising first (M1), second (M2), third (M3) and fourth (M4) mirrors. Each of said four mirrors (M1) (M2) (M3 (M4) provides reflective surfaces, with said third (M3) and fourth (M4) mirrors providing convex and concave reflective surfaces, respectively.

Shown is an input beam (IB) of electromagnetic radiation, (having a specific polarization state), which is directed toward said first (M1) mirror and reflects from said reflective surface thereof, such that a first plane of incidence (P1) is formed between said incident beam (IB) and said beam which is reflected from said reflective surface of said first (M1) mirror. The beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB). Said beam reflected from the reflective surface of said convex third (M3) mirror and that reflected from said reflective surface of said concave fourth (M4) mirror forming a second plane of incidence (P2), said first (P1) and second (P2) planes of incidence being orthogonal to one another. It is noted that in use each of said mirrors (M1), (M2), (M3) and (M4) receives a beam approaching it at an angle of incidence to a surface thereof, and in conjunction with a perpendicular to each said mirror at the point where the beam impinges thereupon, a plane of incidence is defined. in a preferred embodiment it happens that the same Planes are defined by paired mirrors (M1) and (M2), (ie. Plane (P1)), and by paired mirrors (M3) and (M4), (ie. Plane (P2)).

The effect of said four reflections from said reflective surfaces of said four (M1) (M2) (M3) (M4) mirrors is to substantially minimize the effects of all said reflections on the specific polarization state of said input beam, and to direct said output beam (OB) and provide it as a focused beam (FB) onto said sample (SAM) at the point it impinges thereupon.

Said system can involve the first (M1) and (M2) mirrors both having flat reflecting surfaces, or at least one of the first (M1) and second (M2) mirrors has a non-flat reflecting surface, or both the first (M1) and second (M2) mirrors having non-flat reflecting surfaces.

Figure 1B:
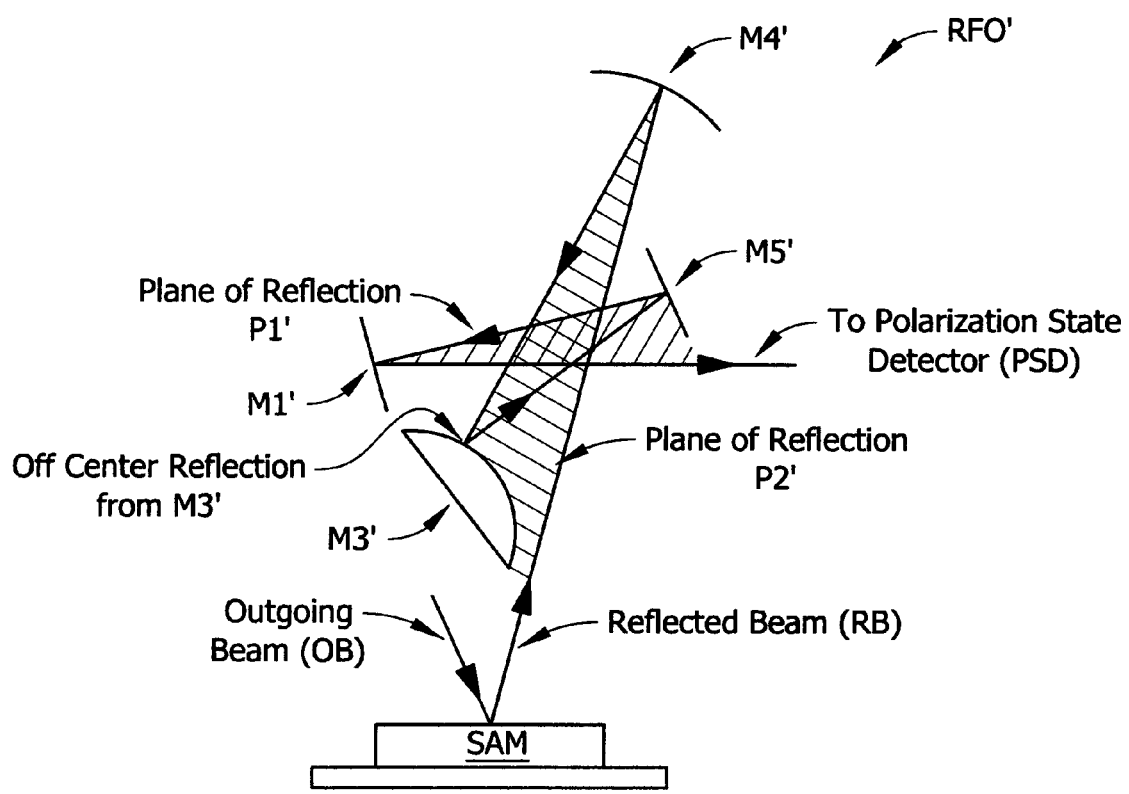
FIG. 1b shows a system for receiving a reflected beam (FB) of electromagnetic radiation a sample (SAM) and directing it toward a Polarization State Detector (PSD).

FIG. 1b shows a system (RFO') for receiving a reflected beam (FB) of electromagnetic radiation a sample (SAM) and directing it toward a Polarization State Detector (PSD) as a collimated beam. Note that FIG. 1b is mirror-image of FIG. 1a as viewed along a vertical line above the location on said Sample (SAM) whereat the Outgoing Beam (OB) impinges thereupon. Also note that identifiers in FIG. 1b are much the same as in FIG. 1a, with Primes "'" added. That is, for instance, Mirrors (M1), (M2), (M3) and (M4) in FIG. 1a correspond to Mirrors (M1'), (M2'), (M3') and (M4') in FIG. 1b. Also identified in FIG. 1b is a Reflected Beam (RB), which is Output Beam (OB) after it reflects from the Sample (SAM). Note that FIG. 1b Planes (P1') and (P2') are orthogonal, as are Planes (P1) and (P2) in FIG. 1a.

Figure 2C:
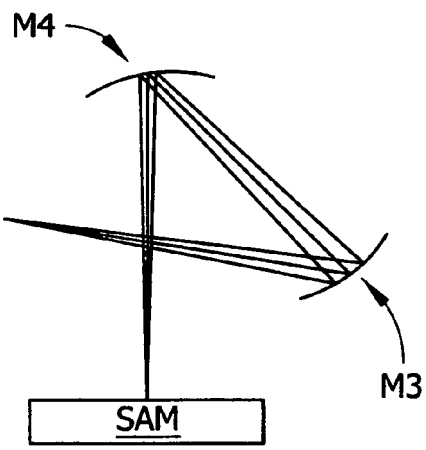
FIGS. 2c and 2d show variations on FIGS. 2a and 2b, but where the convex mirrors (M3) (M3') are replaced with a concave mirrors.
Figure 2D:
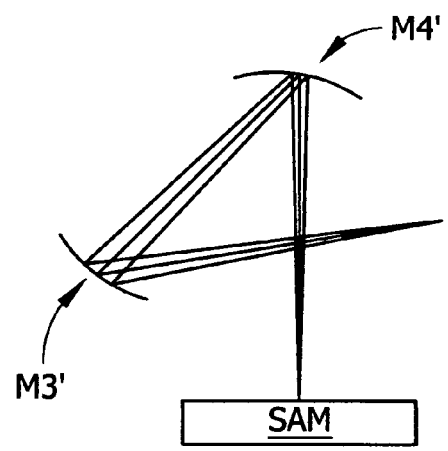
Figure 2E:
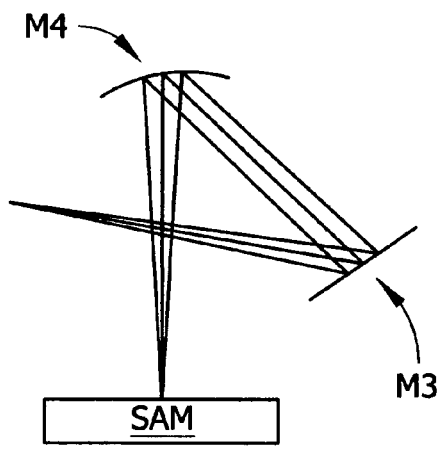
FIGS. 2e and 2f show variations on FIGS. 2a and 2b, but where the convex mirrors (M3) (M3') are replaced with planar mirrors.
Figure 2F:
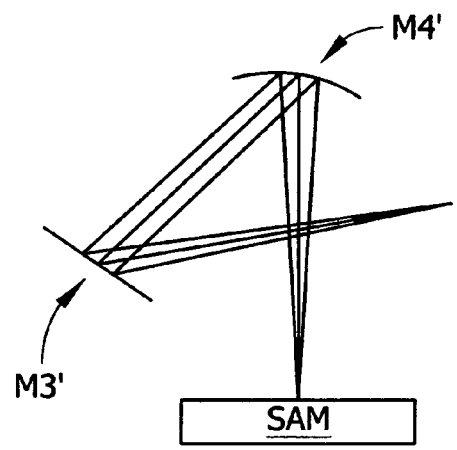
Figure 2G:
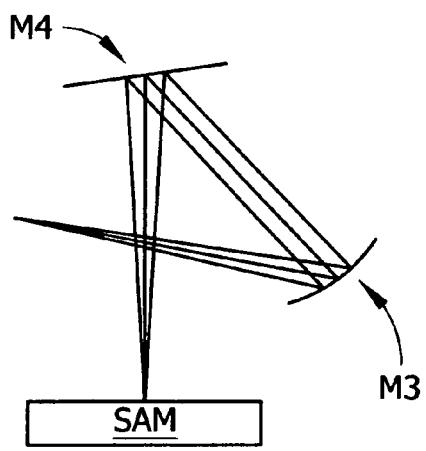
FIGS. 2g and 2h show variations on FIGS. 2a and 2b, but where the convex mirrors (M3) (M3') are replaced with concave mirrors, and concave mirrors (M4) (M4') are replaced with planar mirrors.
Figure 2H:
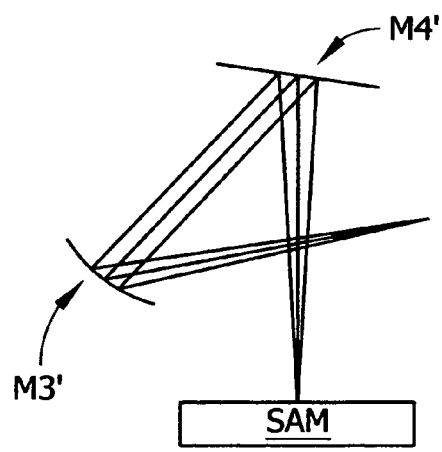

FIG. 2a shows that the off-center reflection from the third convex mirror (M3) provides a "spread-out" beam incident onto the concave fourth (M4) mirror, which fourth (M4) concave mirror serves to focus the spread-out beam onto a sample (SAM) as focused beam (FB). FIG. 2b shows an arrangement for use on the Detector (DET) side of the Sample which compliments that FIG. 2a arrangement on the Source (S) side. The presence of Mirrors (M3') and (M4') direct the beam reflecting from the Sample (SAM) into a Detector (DET) in a manner which compliments that used on the Source (S) side via Mirrors (M3) and (M4). (Note that FIGS. 2a and 2b show very small angles of incidence and reflection and are demonstrative of the present invention system geometry, rather than representative of actual angles of incidence and reflection that might be realized in use. Also, FIG. 2b shows a collimated beam exiting Mirror (M3'), however this is not limiting and a converging or diverging beam can also be present. It is to be understood that FIG. 2b, like FIG. 2a is only partial and shown to identify how a beam reflecting from the Sample (SAM) is reflected and sent to the Detector (DET). In use there will be additional mirrors, ((M1') (M2')) present that are like mirrors (M1) and (M2) in FIG. 1, and there will be planes (P1') and (P2') formed similar to planes (P1) and (P2) between beam reflections from the various mirrors similar to those in FIG. 1a As shown in FIGS. 2a-2h, the Present Invention can comprise a system as in FIGS. 1a and 1b wherein there are, in addition to two planar mirrors, (eg. (M1) (M1') and (M2) (M2') in FIGS. 1a and 1b), there are one convex (M3) and one concave mirror (M4) present, (as per the preferred embodiment), or there are two concave mirrors ((M4) (M4') and (M3) and (M3')) present or wherein there are three planar mirrors (M1) (M1') (M2) (M2') (M3) (M3') present and one concave mirror (M4) (M4'), or three planar mirrors (M1) (M1') (M2) (M2') (M4) (M4') present and one concave mirror (M3) (M3'). In particular, FIGS. 2c and 2d show variations on FIGS. 2a and 2b, but where the convex mirrors (M3) (M3') are replaced with a concave mirrors. FIGS. 2e and 2f show variations on FIGS. 2a and 2b, but where the convex mirrors (M3) (M3') are replaced with planar mirrors. FIGS. 2g and 2h show variations on FIGS. 2a and 2b, but where the convex mirrors (M3) (M3') are replaced with concave mirrors, and concave mirrors (M4) (M4') are replaced with planar mirrors. Note that said system can provide that the reflective properties of each of the mirrors (M1), (M2), (M3) and (M4) are substantially the same, and/or that there are reflective coatings on each of the mirrors (M1), (M2), (M3) and (M4) which are substantially the same based on coating material involved and thickness thereof. While not preferred, these variations are within the scope of the present invention.

FIG. 3a shows, in a more straight forward manner, an ellipsometer system of the present invention which includes the present invention reflective focusing optics (RFO) and (RFO'), described above, in conjunction with Polarization State Generator (PSG) and Polarization State Detector (PSD) elements. Note that FIG. 3b demonstrates the a Polarization State Generator (PSG) typically comprises a Polarizer (P) and can include a Compensator (C). And, FIG. 3c demonstrates that the (PSD) is to be understood to include a Detector (DET) per se. for use in generating Sample (SAM) describing data from an electromagnetic beam entered thereinto from (RFO'). The (PSD) typically comprises an Analyzer (A), and can include an optional Compensator (C). In general a Polarization State Generator (PSG) comprises a Source (S) of an Input Beam (IB) of electromagnetic radiation and a polarizer, and a Polarization State Detector comprises an Analyzer (A) and multi-element Detector (DET).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, with said third (M3) and fourth (M4) mirrors providing convex and concave reflective surfaces, respectively;

such that in use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror;

and such that said beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB); said beam reflected from the reflective surface of said convex third (M3) mirror and that reflected from said reflective surface of said concave fourth (M4) mirror forming a second plane of incidence (P2), said first (P1) and second (P2) planes of incidence being substantially orthogonal to one another;

the effect of said four reflections from said reflective surfaces of said four (M1) (M2) (M3) (M4) mirrors being to substantially minimize the effects of all said reflections on the specific polarization state of said input beam, and to direct said output beam (OB) and provide it as a focused beam (FB) onto said sample (SAM) at the point it impinges thereupon.

2. A system as in claim 1, in which the first (M1) and second (M2) mirrors have flat reflecting surfaces.

3. A system as in claim 1, in which at least one of the first (M1) and second (M2) mirrors has a non-flat reflecting surface.

4. A system as in claim 1, in which both the first (M1) and second (M2) mirrors have non-flat reflecting surfaces.

5. A system as in claim 1, in which the input beam (IB), all reflected beams and the output beam (OB) are spectroscopic.

6. A system as in claim 1 in which the first (P1) and second (P2) planes of incidence are defined by central rays in the reflected beams involved.

7. A system as in claim 1 in which the input (IB), and the various reflected and output (OB) beams are each considered to consist of at least sixteen cross-sectional areas, and in which the calculated overall effect on polarization state of the various reflections from mirrors (M1) (M2) (M3) and (M4) is arrived at by an averaging thereof.

8. A system as in claim 1 in which the angles of incidence of the electromagnetic beams approaching said third (M3) and fourth (M4) mirrors are set to θ1 and θ2 degrees respectively, and in which the angles of incidence of the electromagnetic beams approaching said first (M1) and second (M2) mirrors are each selected from the group consisting of:

a) less than (θ1+θ2)/2;
b) (θ1+θ2)/2 degrees; and
c) greater that (θ1+θ2)/2 degrees.

9. An ellipsometer comprising:
a) a source of a beam of electromagnetic radiation;
b) a polarization state generator;
c) a reflective focusing optics system comprising:
a system for providing a focused beam (FB) of electromagnetic radiation onto a location on a sample (SAM), said system being a reflective optics system (RFO) sequentially comprising first (M1), second (M2), third (M3) and fourth (M4) mirrors, each of said four mirrors (M1) (M2) (M3 (M4) providing reflective surfaces, with said third (M3) and fourth (M4) mirrors providing convex and concave reflective surfaces, respectively;

such that in use an input beam (IB) of electromagnetic radiation having a specific polarization state is directed toward said first (M1) mirror and reflects from said reflective surface thereof, such that a first plane of incidence (P1) is formed between said incident beam (IB) and said beam which is reflected from said reflective surface of said first (M1) mirror;

and such that said beam reflected from the reflective surface of said first (M1) mirror is directed toward said second mirror (M2) and reflects from said reflective surface thereof toward said convex third (M3) mirror, from which it reflects at an off-center location thereon toward said concave fourth (M4) mirror, wherefrom it is reflected by the reflective surface thereof toward said sample (SAM) as a focused (FB) outgoing beam (OB); said beam reflected from the reflective surface of said convex third (M3) mirror and that reflected from said reflective surface of said concave fourth (M4) mirror forming a second plane of incidence (P2), said first (P1) and second (P2) planes of incidence being orthogonal to one another;

the effect of said four reflections from said reflective surfaces of said four (M1) (M2) (M3) (M4) mirrors being to substantially minimize the effects of all said reflections on the specific polarization state of said input beam, and to direct said output beam (OB) and provide it as a focused beam (FB) onto said sample (SAM) at the point it impinges thereupon;

d) a stage (STG) for supporting a sample (SAM); and
e) a polarization state detector (PSD).

10. A system as in claim 9, in which at least one of the first (M1) and second (M2) mirrors has a non-flat reflecting surface.

11. A system as in claim 9, in which both the first (M1) and second (M2) mirrors have non-flat reflecting surfaces.

12. A system as in claim 9, in which the input beam (IB), all reflected beams and the output beam (OB) are spectroscopic.

13. A system as in claim 9, in which the first (P1) and second (P2) planes of incidence are defined by central rays in the reflected beams involved.

14. A system as in claim 9, in which the input (IB), and the various reflected and output (OB) beams are each considered to consist of at least sixteen cross-sectional areas, and in which the calculated overall effect on polarization state of the various reflections from mirrors (M1) (M2) (M3) and (M4) is arrived at by an averaging thereof.

15. A system as in claim 9, in which the angles of incidence of the electromagnetic beams approaching said third (M3) and fourth (M4) mirrors are set to θ1 and θ2 degrees respectively, and in which the angles of incidence of the electromagnetic beams approaching said first (M1) and second (M2) mirrors are each selected from the group consisting of:
 a) less than $(\theta 1+\theta 2)/2$;
 b) $(\theta 1+\theta 2)/2$ degrees; and
 c) greater that $(\theta 1+\theta 2)/2$ degrees.

16. A system as in claim 1 or 9, In which the reflective properties of each of the mirrors (M1), (M2), (M3) and (M4) are substantially the same.

17. A system as in claim 1 or 9, in which each of the mirrors (M1), (M2), (M3) and (M4) comprises substrate of one material and a coating thereupon of at least one different material.

18. A system as in claim 1 or 9, which further comprises additional fifth (M1'), sixth (M2'), seventh (M3') and eighth (M4') mirrors arranged in a substantially mirror image with respect to mirrors (M1), (M2), (M3) and (M4), said mirrors (M1'), (M2'), (M3') and (M4') serving to and direct said beam into a polarization state detector (PSD).

\* \* \* \* \*